United States Patent [19]
Yoshimoto

[11] Patent Number: 5,299,561
[45] Date of Patent: Apr. 5, 1994

[54] SUCTION CONTROL APPARATUS FOR AN ENDOSCOPE

[75] Inventor: Yosuke Yoshimoto, Tokyo, Japan

[73] Assignee: Olympus Optical Co., Ltd., Tokyo, Japan

[21] Appl. No.: 916,913

[22] Filed: Jul. 20, 1992

[30] Foreign Application Priority Data

Aug. 21, 1991 [JP] Japan .................. 3-209299

[51] Int. Cl.[5] .......................... A61B 1/00
[52] U.S. Cl. ................................. 128/4
[58] Field of Search ............... 128/5, 4; 604/30, 33, 604/118, 119, 249; 251/32.5

[56] References Cited

U.S. PATENT DOCUMENTS

| | | |
|---|---|---|
| 4,198,958 | 4/1980 | Utsugi ........................ 128/5 |
| 4,412,531 | 11/1983 | Chikashige . |
| 4,562,830 | 1/1986 | Yabe . |
| 4,736,732 | 4/1988 | Shimonaka et al. . |
| 4,794,913 | 1/1989 | Shimonaka et al. . |

FOREIGN PATENT DOCUMENTS

| | | | |
|---|---|---|---|
| 55394 | 7/1982 | European Pat. Off. ........... 128/4 |
| 58-54924 | 4/1983 | Japan . |
| 60-15523 | 5/1985 | Japan . |
| 63-203127 | 8/1988 | Japan . |
| 63-214228 | 9/1988 | Japan . |

Primary Examiner—Richard J. Apley
Assistant Examiner—Karen A. Jalbert
Attorney, Agent, or Firm—Frishauf, Holtz, Goodman & Woodward

[57] ABSTRACT

An endoscope includes a cylinder body having an opening leading to a suction channel and an opening of the suction channel leads to a suction device both of side bath of these openings are provided in an adjacent, parallel relation. A cap member is detachably mounted on the cylinder body and is made of an elastic member. A piston is provided on the cap member to allow one of the openings to be opened or closed through the movement of the piston. A suction control unit thus achieved has a simpler arrangement and enables easy and positive cleaning.

22 Claims, 5 Drawing Sheets

SUCTION CONTROL APPARATUS FOR AN ENDOSCOPE

BACKGROUND OF THE INVENTION

1. Field of the Invention

The present invention relates to an endoscope having a suction control unit for sucking, for example, waste in a body cavity, cleaning water injected, etc., and removing them.

2. Description of the Related Art

Published Examined Japanese Utility Model 128 Registration corresponding to U.S. Pat. No. 4,412,531 and Published Unexamined Japanese Patent Application 63-214228 disclose known ordinary endoscopes whose suction control unit includes a cylinder incorporated into a control section and a control piston inserted into the cylinder and having a suction tube leading to a suction unit and suction channel for the endoscope which are connected to the cylinder.

One end of the suction channel and one end of the suction tube are connected in a mutually orthogonal relation to the cylinder. For this reason, upon the cleaning of the suction tube, a cleaning brush is externally pushed into the cylinder so as to force waste into the cylinder. Then the brush is inserted via the opening side of the cylinder to allow the waste to be discharged out of the distal end of an insertion section.

If a sequence of operation is wrongly done, it is sometimes impossible to completely discharge remaining waste out of the whole tube. Further, the operation sequence is also important from the standpoint of preventing the infection of diseases, etc. Since the suction channel and suction tube are connected in an orthogonal relation to the axial direction of the cylinder, it is cumbersome to perform a cleaning operation by the cleaning brush.

Published Unexamined Japanese Patent Application No. 63-203127 discloses an endoscope having a suction control unit of such a type that a suction channel and a suction tube leading to a suction unit are provided in a parallel relation, but that they have to be individually connected to a corresponding connector body. The arrangement includes, in addition, an elastic control valve, etc., and becomes complex and hard to clean by a cleaning brush. In particular, the control valve per se is liable to be soiled with deposited waste, thus leaving something to be improved.

SUMMARY OF THE INVENTION

It is accordingly the object of the present invention to provide an endoscope whose suction control unit is simpler in arrangement and easier to clean than a conventional counterpart.

According to the present invention, there is provided an endoscope including a suction control unit for controlling communication between a fluid channel leading to a suction source and a fluid channel extending in an insertion section insertable into a cavity of an object, the endoscope comprising:

the insertion section;

a control section for operating the insertion section outside the object;

a first fluid channel extending from the insertion section to the control section;

a second fluid channel provided in the control section and connectable to the suction source;

a control body provided at the control section and having an outer surface, the control body having a first hole having one end connected to the first fluid channel and the other end, as a first opening, opened outwardly of the control body, the first hole having an axis, and a second hole having one end connected to the second fluid channel and the other end, as a second opening, opened outwardly of the control body, the second hole having an axis, wherein the first and second openings are provided at the outer surface of the control body in an adjacent relation;

a cap member detachably mounted on the control section and covering the outer surface of the control body with a given spacing left therebetween;

first means for communicating between the first and second holes via the given spacing; and second means for controlling communication to be made by the first means.

According to the present invention, the suction control unit is simpler in structure and inexpensive. Since the two independent channel openings are exposed at the outer surface of the control body in an adjacent relation, the endoscope can be readily and positively cleaned by a brush and minimize a risk of infection. As a result, the endoscope can be kept under a sanitary condition.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
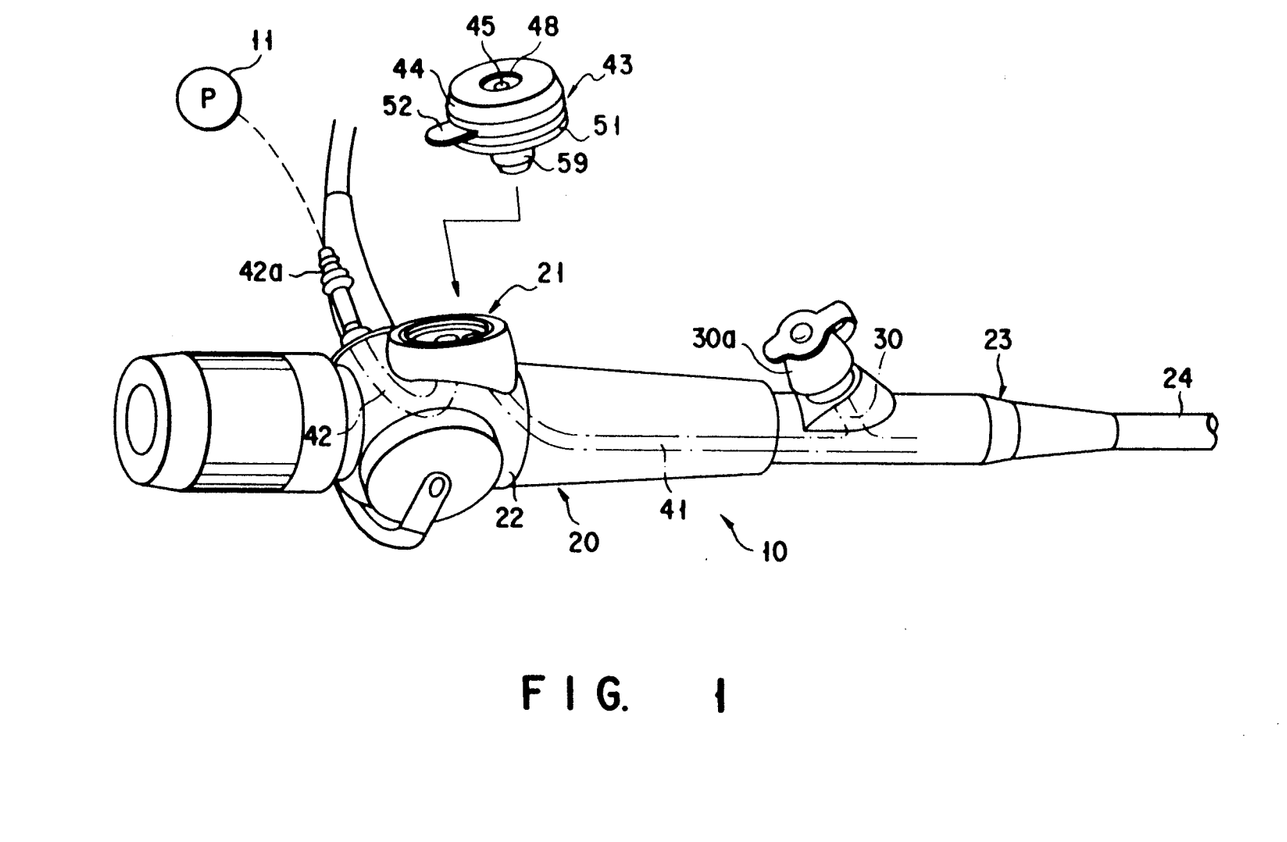
FIG. 1 is a perspective view showing a suction control unit in a control section of an endoscope according to a first embodiment of the present invention with a cap member of the endoscope removed.

FIGS. 1 to 4 show a first embodiment of the present invention. FIG. 1 shows a control section 20 of an endoscope 10 and its neighborhood. A suction control unit 21 as will be set out in detail below is provided at the control section 20. An insertion section 24 is connected to a body 22 of the control section 20 by a connection section 23 as will be set out below. The insertion section 24 of the endoscope 10 is insertable into a body cavity of a human subject.

The arrangement of the connection section 23 is as shown in FIG. 4. A flexible tube 25 of the insertion section 24 comprises a spiral-tube, a meshed tube and an outer skin. The base end edge portion of the flexible tube 25 is clamped to the outer periphery of one end portion of a cylindrical connector 26 by being pushed by a pressing ring 28 which is clamped by a clamping ring 27. One end portion of a cylindrical, electrically insulating member 29 is fitted over the outer periphery of the other end portion of the connector 26. An inner hole 29a of the insulating member 29 is oblong in cross-section as viewed in an up/down direction in FIG. 4C and is eccentrically located in a down direction.

Figure 4A:
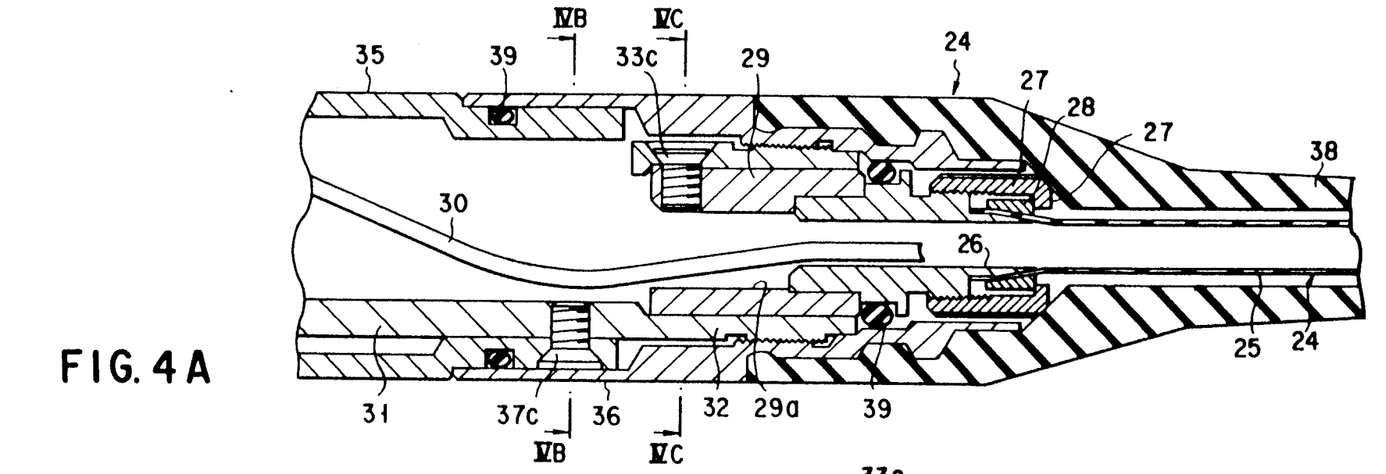
FIG. 4A is a cross-sectional view showing a connection section between the control section and an insertion section in the first embodiment.
Figure 4B:
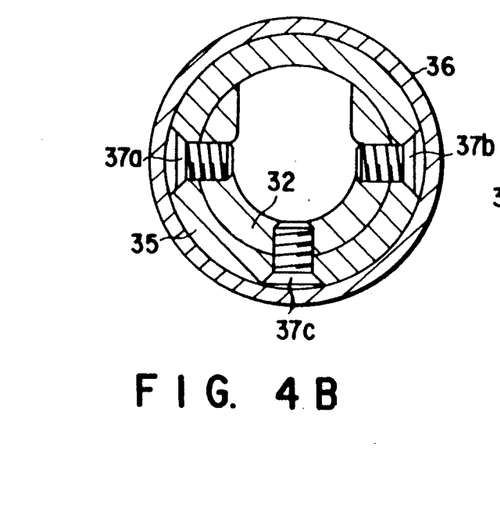
FIG. 4B is a cross-sectional view as taken along line IVB—IVB in FIG. 4A.

The insulating member 29 is partially cut away at its lower portion with its upside wall portion providing a thicker wall and its downside wall portion providing a thinner wall. Thus a greater space is created for a passage into which a channel tube 30 is inserted from an upper side down toward the distal end side. As a result, the channel tube 30 can be readily guided without any undue burden.

Figure 4C:
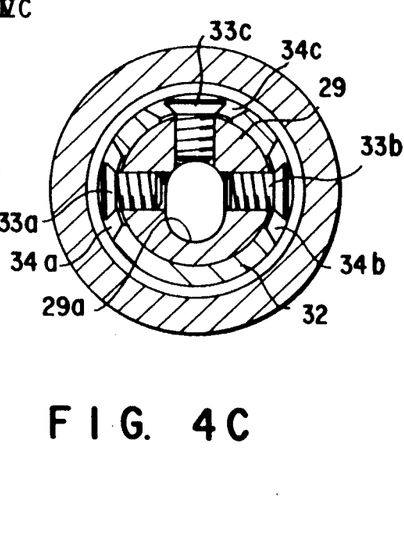
FIG. 4C is a cross-sectional view as taken along line IVC—IVC in FIG. 4A.

The insulating member 29 is fitted into the coupling cylindrical section 32 provided on the forward end portion of a metal frame 31 at the body 22 of the control section 20 and is fixed there by three head-equipped screws 33a, 33b and 33c. These screws are threadably inserted into the insulating member 29 from left and right and upper directions as shown in FIG. 4C.

Figure 4D:
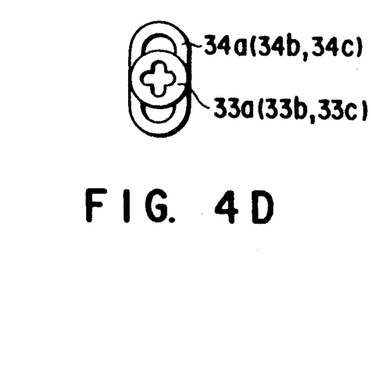
FIG. 4D is a front view showing a head-equipped screw in a corresponding countersunk hole in the first embodiment.

The respective screws 33a, 33b and 33c are separately inserted into the coupling cylindrical section 32 at those areas where corresponding countersunk holes 34a, 34b and 34c are provided. These countersunk holes are so provided as to have their longer sides formed along the outer circumference of the coupling cylindrical section 32 as shown in FIG. 4D. Since, upon the connection of the insertion section 24 to the control section 20, the insertion section 24 can be adjusted to its fixing position while being rotated relative to the control section 20 to some extent, it is possible to readily and properly orient the direction of the endoscope relative to an image guide's image.

The coupling cylindrical section 32 at the forward end portion of the frame 31 of the control section 20 is inserted into an outer casing 35 at the body 22 of the control section 20 with a connection tube 36 threadably fixed on the outer surface of the coupling cylindrical section 32. The outer casing 35 is fastened to the frame 31 by head-equipped screws 37a, 37b and 37c. One end of a bend-preventing tube 38 comprised of an elastic member is fitted over the forward end portion of the connection tube 36. Reference numeral 39 in FIG. 4A shows a packing for sealing purpose.

Figure 2:
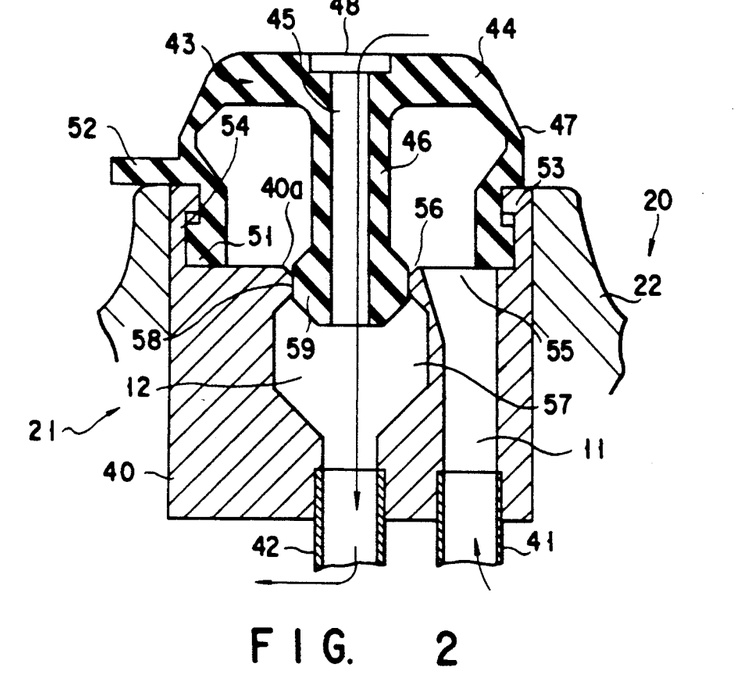
FIG. 2 is a cross-sectional view showing the first embodiment with the suction control unit in a normal state.
Figure 3:
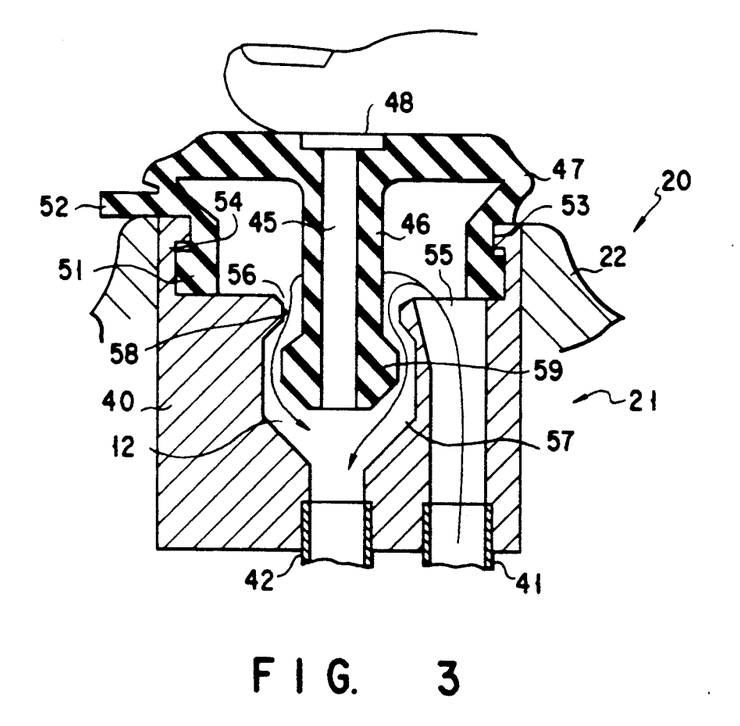
FIG. 3 is a cross-sectional view showing the first embodiment with the suction control unit in a sucked state.

The suction control unit 21 is so configured as shown in FIGS. 2 and 3. The control unit 21 has a cylinder body 40 as a control body mounted on the body 22 of the control unit 20. To the cylinder body 40 are connected a suction channel (first fluid passage) 41 leading to the insertion section 24 and a suction channel (second fluid passage) 42 leading to a suction connector 42a for making a connection to a suction pump 11A serving as an outer suction device. The suction channel 41 provides a fluid passage extending from the control section 20 to the insertion section 24 at an inner area of the control section 20 partway of an treating instrument insertion channel which is provided by a channel tube 30 leading to a forceps insertion connector 30a, the fluid passage joining the treating instrument insertion channel.

As shown in FIG. 2, a cap member 44 is detachably mounted on the outer end portion of the cylinder body 40 and serves as a suction control button 43. The cap member 44 is oblong-cylindrical in configuration with a bottom and is made of an elastic material, such as rubber. At the cap member 44, a piston 46 having a leakage passage 45 leading to an outer atmosphere is inwardly projected beyond the central portion of the bottom of the cap member 44. A boundary area 47 where the outer peripheral section of the bottom wall portion merges with the cylindrical section of the cap member 44 is thinner than the rest of the cap member 44 to allow the boundary area to be elastically deformed when a finger button section 48 constituted by the bottom wall section is depressed.

A flange 51 is provided around the whole circumferential opening inner portion of the cap member 44 for mounting to the cylinder body 40. A knob 52 is provided on the cap member 44 so that the member 44 is readily detachable. An upright wall section 54 is provided along the whole outer peripheral area of the cylinder body 40 beyond an outer surface 40a. A flange 53 is projected from the inner end edge portion of the upright wall section 54 s that the flange 53 is latched to the flange 51 of the suction control button 43. The outer surface 40a of the cylinder body 40 is surrounded with the upright wall section 54 with a spacing over the outer surface 40a being covered with the cap member 44.

First and second holes 11 and 12 are adjacently provided in the cylinder body 40 in a parallel relation with one open end of the first hole 11 communicating with the suction channel 41 and one open end of the second hole 12 communicating with the suction channel 42. The other open end of the first hole 11 is outwardly opened, as a channel opening 55, at the outer surface 40a and the other open end of the second hole 12 is outwardly opened at the outer surface 40a and provides the cylinder's opening area 56 leading to the suction channel 42. The cylinder's opening area 56 is located at the central area of the cylinder body 40 and the channel opening 55 is eccentrically provided toward the major axis of the outer peripheral side of the cylinder body 40. The channel opening 55 and cylinder opening area 56 have their center axes extended in a parallel, side-by-side relation and are opened outwardly of the control section 20. The channel opening 55 and cylinder opening area 56 have their center axes extended in a parallel relation to the center axis of the cylinder body 40. A space over the outer surface 40a of the cylinder body 40, being covered with the cap member 44, communicates with the channel opening 55 and cylinder's opening area 56.

The open end of the cylinder's opening area 56 and its inner diameter are smaller than an inward space 57 and a small diameter inner opening 58 is somewhat smaller than the outer diameter of a large-diameter section 59 of the piston 46. The base portion of the piston 46 is made smaller than the small diameter opening 58. A large-diameter section 59 of the piston 46 is normally intimately penetrated into the small-diameter opening, as shown in FIG. 2, in which case the large-diameter section 59 of the piston 46 is fitted around the inner surface of the small-diameter opening 58 in a water-tight fashion.

The operation of the suction control unit 21 in the endoscope will be explained below.

FIG. 2 shows a non-operative state of the suction control unit 21. In this state, an outer atmosphere is sucked, via the leakage passage 45, into the suction channel 42 under a suction force by the external suction device. The cylinder's opening area 56 is closed by the piston 46, blocking communication between the suction channel 41 and the suction channel 42.

FIG. 3 shows an operative state of the suction control unit 21. When the finger button section 48 of the suction control button 43 is downwardly depressed against an elastic force of the button 4 while blocking the opening of the leakage passage 45 by the operator's finger, the piston 46 is downwardly moved, opening the cylinder's opening section 56 to allow communication to be established between the suction channel 41 and the suction channel 42. Then suction is created through the suction channel 41 on the insertion section 24 side. Upon the release of the finger away from the opening of the leakage passage 45, the suction control button 43 is returned back to a ready state, as shown in FIG. 2, under its elastic recovery.

According to the present embodiment thus configured, the first hole leading to the suction channel is provided in the cylinder body in a parallel relation to the second hole leading to the suction device side and the opening/closing piston is provided at the cap member which is detachably mounted on the cylinder body. This arrangement ensures a simpler, inexpensive suction control unit. The present endoscope involves no backflow of waste, etc., and prevents their external leakage. Further, a fine adjustment can be made by controlling a push on the cap member and hence a suction level. Since the two independent holes are opened at the cylinder body in a parallel relation as already set out above, cleaning can be readily and positively made by a brush without involving any problem as encountered upon the use of the brush. Sanitary cleaning can also be made by the brush without any risk of infection.

Figure 5:
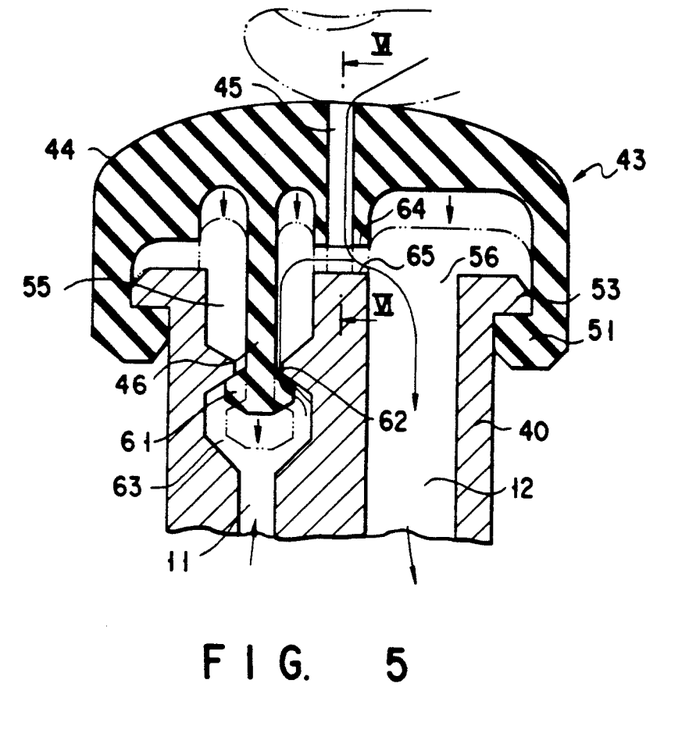
FIG. 5 is a cross-sectional view showing a suction control unit in a second embodiment of the present invention.
Figure 6:
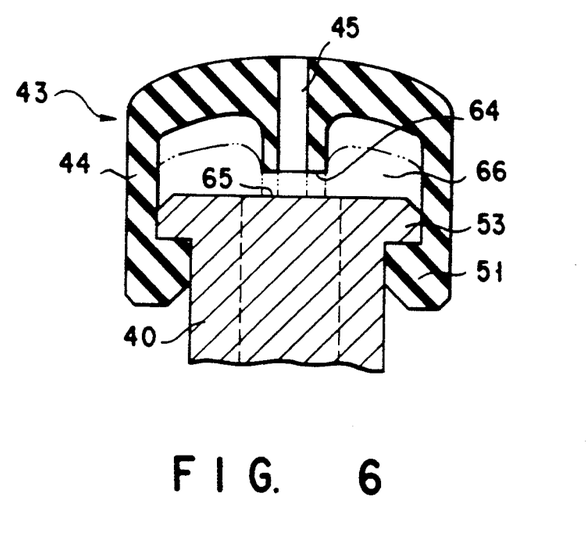
FIG. 6 is a cross-sectional view as taken along line VI—VI in FIG. 5.

FIGS. 5 and 6 show a second embodiment of the present invention. In the second embodiment, a piston 46 is fitted into a channel opening 55 side of a suction channel 41 while, in the first embodiment, the piston 46 is fitted into the cylinder's opening area 56 leading to the suction channel 42. The leakage passage 45 is located at substantially the center area of a suction control button 43 and the piston 46 is eccentrically located toward the outer side and coaxially extends in an opposed relation to the channel opening 55.

The channel opening 55 is provided as a small-diameter section 62 which is made smaller in diameter than a large-diameter section 61 formed at the forward end of the piston 46 and larger in diameter than a base end portion of the piston 46. The large-diameter section 61 of the piston 46 is penetrated into an internal space 63 at the channel opening 55. Normally (in the non-sucked state) the large-diameter section 61 of the piston 46 is intimately abutted against the small-diameter section 62 at the channel opening 55 to block the channel opening 55 of the first hole 11.

An area of the suction control button where the leakage passage 45 is formed is projected as a projection whose forward end 64 oppositely faces an outer top end, that is a top flat surface, of a cylinder body 40. The forward end 64 of the projection is normally spaced away from the top flat surface 65 of the cylinder body 40 to provide a gap therebetween as shown in FIG. 5. Upon the pushing of the suction control button 43, the forward end of the projection of the control button 43 abuts against the top flat surface 65 of the cylinder body 40 to restrict an amount of push by the suction control button 43. A communication passage 66 is provided on both sides of the forward end 64 of the projection through which the leakage passage 45 is provided. Even when the forward end 64 is abutted against the top flat surface 65 of the cylinder body 40, communication is allowed to be made between the channel opening 55 and the cylinder's opening area 56.

At the non-sucking time, the large-diameter section 61 of the piston 46 blocks the channel opening 55 and an outer atmosphere is sucked via the leakage passage 45 into the suction channel 42.

When suction is to be created, the outer open end of the leakage passage 45 is blocked by the operator's finger and the suction control button 43 is downwardly depressed as indicated by a dash dot line in FIG. 5 and FIG. 6, the forward end 64 of the projection through which the leakage passage 45 is provided abuts against the top flat surface 65 of the cylinder body. The large-diameter section 61 of the piston 46 is penetrated away from the channel opening 55 into an inward space 63 to set the channel opening 55 in an opened state. Further, the channel opening 55 communicates with the cylinder's opening area 56 via the communication passage 66. For this reason, waste is sucked via the communication passage 66 on both the sides of the leakage passage 45 as shown in FIG. 6. At this time, the leakage passage 45 is set in a completely shielded state, thus eliminating a risk of the operator's finger being soiled due to a backflow of waste.

Where the suction control button 43 is detached away from the cylinder body 40, the large-diameter section 61 of the piston 46 is released away from the small-diameter section 62 at the channel opening 55 under its own elastic deformation.

Figure 7:
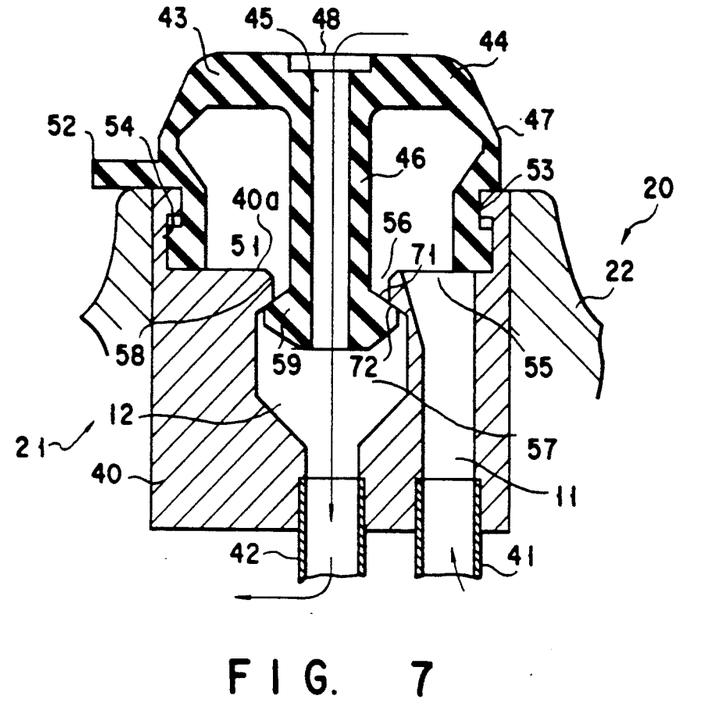
FIG. 7 is a cross-sectional view showing a suction control device in a third embodiment of the present invention.
Figure 8:
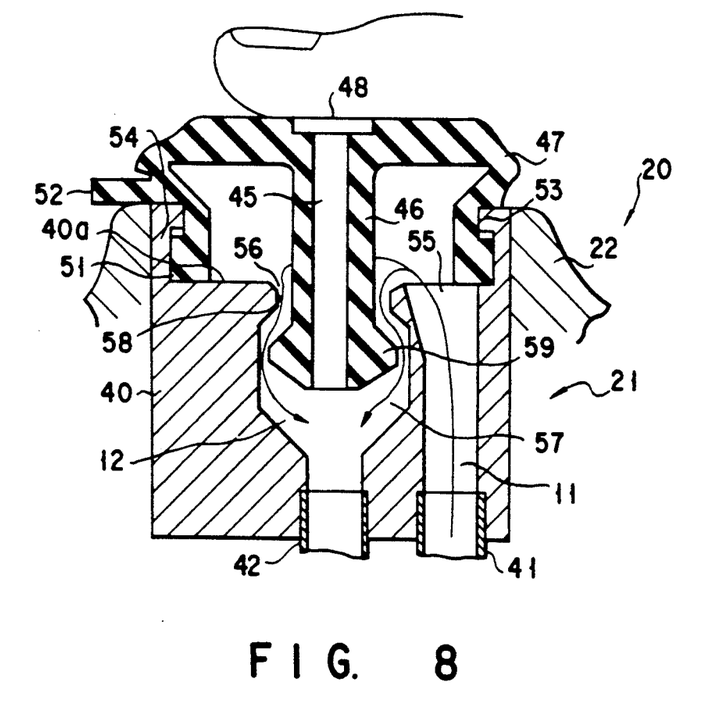
FIG. 8 is a cross-sectional view showing the third embodiment with the suction control device in a sucked state.

FIGS. 7 and 8 show a third embodiment of the present invention. Although, in the first embodiment, the large-diameter section 59 of the piston 46 has been explained as being fitted around the inner surface of the small-diameter opening 58 in a liquid-tight fashion, the third embodiment is of such a type that the tapered surface 71 provided at the upper end edge of the large-diameter section 59 of the piston 46 abuts against a tapered valve seat 72 provided at the lower side edge of a small-diameter section 58, the tapered section 71 abutting against the tapered valve seat 72 to provide a valve means. When the tapered surface 71 abuts against the valve seat 72 with the suction control button 43 not depressed, communication between holes 11 and 12 is shut off as shown in FIG. 7. When, on the other hand, the tapered surface 71 is spaced apart from the valve seat 72 with the suction control button 43 depressed, communication is created between these holes 11 and 12 as shown in FIG. 8. The third embodiment is substantially the same as the first embodiment except for those immediately set out above.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An endoscope including a suction control unit for controlling communication between a fluid channel leading to a suction source and fluid channel extending in an insertion section, the insertion section being insertable into a cavity of an object, the endoscope comprising:

the insertion section;
   a control section for operating the insertion section, the control section being adapted to be positioned outside of the object;
   a first fluid channel extending from the insertion section to the control section;
   a second fluid channel provided in the control section, the second fluid channel being connectable to the suction source;
   a control body provided at the control section, the control body having:
     an outer surface;
     a first hole having two end portions and an axis, with one end portion being coupled in fluid communication with the first fluid channel; and
     at its other end portion, a first opening which is opened outwardly of the control body; and
     a second hole having two end portions and an axis, with one end portion being coupled to the second fluid channel; and
     at its other end portion, a second opening which is opened outwardly of the control body;
   and wherein the first and second openings are adjacent to each other at the outer surface of the control body;
   a cap member detachably mounted on the control section, the cap member covering the outer surface of the control body so that a given space is formed therebetween;
   control means for selectively placing the first and second holes in fluid communication with each other via said given space, the control means including a piston member inserted to be movable with a stroke-like motion in a given direction into the second hole to selectively open and close the second hole in cooperation with walls defining the second hole;
   the piston member having:
     a leak hole that is in fluid communication with an outer atmosphere; and
     wherein the leak hole extends substantially along the given direction of the stroke-like motion of the piston member into the second hole.

2. The endoscope according to claim 1, wherein the axes of the first and second holes extend in said control body substantially parallel to each other.

3. The endoscope according to claim 1, wherein the axes of the first and second holes extend in said control body at a given small angle relative to each other.

4. The endoscope according to claim 1, wherein:
   the cap member has:
     a finger-operable button section; and
     a section that is elastically deformable upon a depression thereof by a finger of an operator; and
   the piston member is movable when the button section is depressed and moves with the stroke-like motion between an open position and a closed position in the second hole based on a position thereof when the button section is depressed and a position to which the button section returns after an operation thereof.

5. The endoscope according to claim 4, wherein the cap member and the piston member form an elastic member which is formed as one integral unit.

6. The endoscope according to claim 4, wherein the cap member has:
   a leakage hole which extends through the piston member from the finger-operable button section thereof;
   a first end portion of the leakage hole leads to the second opening of the second hole; and
   a second end portion of the leakage hole is opened outside an outer surface of the button section, the second end portion of the leakage hole is blockable by a finger of an operator.

7. The endoscope according to claim 1, wherein:
   the piston member has a first diameter section and a second diameter section, said second diameter section being larger in diameter than said first diameter section; and
   a valve seat is provided at an opening end edge portion of the second hole, into which the piston member is inserted, said valve seat has a section thereof that is in intimate contact with an outer periphery of the second diameter section of the piston member;
   a space is formed in at least a portion of the second hole, said second hole having an inner diameter that is larger than an outer diameter of the second diameter section of the piston member so that a fluid communication between the first and second holes is shut off when the second diameter section of the piston member is positioned on the valve seat, said fluid communication being established when the second diameter section of the piston member is moved away from the valve seat into the space.

8. The endoscope according to claim 1, wherein:
   the piston member has a first diameter section and a second diameter section, said second diameter section being larger in diameter than said first diameter section;
   a cylinder opening area is provided which has a valve seat provided at an inner end portion of the second opening of the second hole, said second opening of the second hole being smaller in diameter than the second diameter section of the piston member and being larger in diameter than the first diameter section of the piston member; and
   a space is formed in at least a portion of the cylinder opening area, said cylinder opening area having an inner diameter that is larger than the second diameter section of the piston member, so that a fluid communication between the first and second holes is shut off when the second diameter section of the piston member abuts against the valve seat and a fluid communication is established when the second diameter section of the piston member is moved away from the valve seat into the space.

9. The endoscope according to claim 1, wherein the piston member of the control means is movable with said stroke-like motion to open or close the second hole in association with walls defining the second hole.

10. An endoscope including a suction control unit for controlling communication between a fluid channel leading to a suction source and fluid channel extending in an insertion section, the insertion section being insertable into a cavity of an object, the endoscope comprising:

the insertion section;
a control section for operating the insertion section, the control section being adapted to be positioned outside of the object;
a first fluid channel extending from the insertion section to the control section;
a second fluid channel provided in the control section, the second fluid channel being connectable to the suction source;
a control body provided at the control section, the control body having:
an outer surface;
a first hole having two end portions and an axis, with one end portion being coupled in fluid communication with the first fluid channel; and
at its other end portion, a first opening which is opened outwardly of the control body; and
a second hole having two end portions and an axis, with one end portion being coupled to the second fluid channel; and
at its other end portion, a second opening which is opened outwardly of the control body;
and wherein the first and second openings are adjacent to each other at the outer surface of the control body;
a cap member detachably mounted on the control section, the cap member covering the outer surface of the control body so that a given space is formed therebetween;
control means for selectively placing the first and second holes in fluid communication with each other, said control means including a piston member, said piston member being movable with a stroke-like motion in a given direction into the second hole to selectively open and close the second hole in cooperation with walls defining the second hole, said control means including:
means for enabling a fluid communication between the first and second holes via the given space;
said piston member having:
first and second end portions, the first end portion of said piston member being inserted into said second hole, to be movable with said stroke-like motion into the second hole;
a finger-operable button section provided at the second end portion thereof; and
a leak hole that is in fluid communication with an outer atmosphere; and
wherein the leak hole of the piston member extends substantially along the given direction of the stroke-like motion of the piston member into the second hole;

a valve seat provided at the second hole into which the first end portion f said piston member is inserted, a fluid communication being controlled between the first and second holes by the valve seat and the piston member; and wherein
the cap member has:
a leakage hole which extends through the piston member from the finger-operable button section thereof: and
a first end portion of the leakage hole leading to the opening of the second hole where the valve seat is provided;
a second end portion of the leakage hole being opened outside a surface of the button section of the piston member and the first end portion of the leakage hole being opened to a suction side of the suction source with the valve seat as a reference and the second end portion of the leakage hole being blockable by a finger of an operator.

11. The endoscope according to claim 10, wherein the axes of the first and second holes extend in said control body substantially parallel to each other.

12. The endoscope according to claim 10, wherein the axes of the first and second holes extend in said control body at a given small angle relative to each other.

13. The endoscope according to claim 10, wherein:
the cap member is provided continuous with the finger-operable button section of the piston member, and has a deformable section that is elastically deformable upon a depression of the finger-operable button section; and
the piston member is movable between a position when the button section is depressed and a position to which the cap member returns after a deformation of the deformable section.

14. The endoscope according to claim 13, wherein the cap member and piston member form an elastic member which is formed as one integral unit.

15. The endoscope according to claim 10, wherein:
the piston member has a first diameter section and a second diameter section, said second diameter section being larger in diameter than said first diameter section;
a cylinder opening area is provided that has a valve seat provided at the opening of the second hole in which the piston member moves, the cylinder opening area having a section thereof that is in intimate contact with an outer periphery of the second diameter section of the piston member and is larger in diameter than the first diameter section of the piston member;
a space is formed in at least a portion of the second opening of the second hole in which the piston member moves; and
the second opening of the second hole has an inner diameter that is larger in diameter than an outer diameter of the second diameter section of the piston member so that fluid communication between the first and second holes is shut off when the second diameter section of the piston member is positioned on the valve seat and fluid communication is established when the second diameter section of the piston member is moved away from the valve seat into the space.

16. The endoscope according to claim 10, wherein:
the piston member has a first diameter section and a second diameter section, said second diameter section being larger in diameter than the first diameter section;

a valve seat is provided at an inner end portion of the second hole, said second opening of said second hole is smaller in diameter than the second diameter section of the piston member and is larger in diameter than an outer diameter of the first diameter section of the piston member; and a space if formed in at least a portion of the second hole in which the piston member moves, said second hole having an inner diameter that is larger than an outer diameter of the second diameter section of the piston member so that a fluid communication between the first and second holes is shut off when the second diameter section of the piston member abuts against the valve seat and said fluid communication is established when the second diameter section of the piston member is moved away from the valve seat into the space.

17. An endoscope including a suction control unit for controlling a communication between a fluid channel leading to a suction source and a fluid channel extending in an insertion section, the insertion section being insertable into a cavity of an object, the endoscope comprising:

the insertion section;

a control section for operating the insertion section, the control section being positioned outside of the object;

a first fluid channel extending from the insertion section to the control section;

a second fluid channel provided in the control section, the second fluid channel being connectable to the suction source;

a control body provided at the control section, the control body having:

an outer surface;

a first hole having two end portions and an axis, with one end portion being coupled in fluid communication with the first fluid channel; and at its other end portion, a first opening which is opened outwardly of the control body; and a second hole having two end portions and an axis, with one end portion being coupled to the second fluid channel; and at its other end portion, a second opening which is opened outwardly of the control body;

and wherein the first and second openings are adjacent to each other at the outer surface of the control body;

a cap member detachably mounted on the control section, the cap member covering the outer surface of the control body so that a given space is provided therebetween;

first means for enabling a fluid communication between the first and second holes via the given space;

second means for controlling a fluid communication to be enabled by the first means;

the cap member having a leak hole for allowing a fluid communication to be established between an outer atmosphere and a communication space; and an open end side of the leak hole on the communication space side thereof being provided such that the open end side of the leak hole confronts the outer surface of the control body of the control section so that, when the cap member is pushed, the open end side of the leak hole is closed by the outer surface of the control body of the control section to allow a communication between the first and second holes to be established through the communication space thereby to provide said control means.

18. The endoscope according to claim 17, wherein the axes of the first and second holes extend in said control body substantially parallel to each other.

19. The endoscope according to claim 17, wherein the axes of the first and second holes extend in said control body at a given small angel relative to each other.

20. The endoscope according to claim 17, wherein: the cap member has:

a finger-operable button section; and a section that is elastically deformable upon a depression thereof by a finger of an operator; and further comprising:

a piston member that is movable when the button section is depressed, said piston member moving with a stroke-like motion between an open position and a closed position in the second hole based on a position thereof when the button section is depressed and a position to which the button section returns after an operation thereof.

21. The endoscope according to claim 17, further comprising:

a piston member having a first diameter section and a second diameter section, said second diameter section being larger in diameter than said first diameter section; and a valve seat provided at an opening end edge portion of the second hole, into which the piston member is inserted, said valve seat having a section thereof that intimately contacts an outer periphery of the second diameter section of the piston member; and a space formed in at least a portion of the second hole, said second hole having an inner diameter that is larger than an outer diameter of the second diameter section of the piston member, so that a fluid communication between the first and second holes is shut off when the second diameter section of the piston member is positioned on the valve seat, said fluid communication being established when the second diameter section of the piston member is moved away from the valve seat into the space.

22. The endoscope according to claim 17, further comprising:

a piston member having a first diameter section and a second diameter section, said second diameter section being larger in diameter than said first diameter section;

a cylinder opening are having a valve seat provided at an inner end portion of the second opening of the second hole, said second opening of the second hole being smaller in diameter than the second diameter section of the piston member and being larger in diameter than the first diameter section of the piston member; and a space formed in at least a portion of the cylinder opening area, said cylinder opening area having an inner diameter that is larger than the second diameter section of the piston member, so that a fluid communication between the first and second holes is shut off when the second diameter section of the piston member abuts against the valve seat and a fluid communication is established when the second diameter section of the piston member is moved away from the valve seat into the space.

* * * * *